(12) United States Patent
Goble et al.

(10) Patent No.: US 6,929,641 B2
(45) Date of Patent: *Aug. 16, 2005

(54) ELECTROSURGICAL SYSTEM

(75) Inventors: Coliin C. O. Goble, Surrey (GB); Scott T. Latterell, Minneapolis, MN (US); Douglas S. Wahnschaffe, Otsego, MN (US)

(73) Assignee: Gyrus Medical Limited, Cardiff (GB)

(*) Notice: Subject to any disclaimer, the term of this patent is extended or adjusted under 35 U.S.C. 154(b) by 197 days.

This patent is subject to a terminal disclaimer.

(21) Appl. No.: 10/378,657

(22) Filed: Mar. 5, 2003

(65) Prior Publication Data

US 2003/0163123 A1 Aug. 28, 2003

Related U.S. Application Data

(63) Continuation-in-part of application No. 10/228,284, filed on Aug. 27, 2002, now Pat. No. 6,878,148.
(60) Provisional application No. 60/314,650, filed on Aug. 27, 2001.

(30) Foreign Application Priority Data

May 27, 2002 (GB) .............................................. 0212162

(51) Int. Cl.$^7$ .............................................. A61B 18/14
(52) U.S. Cl. .............................. 606/37; 606/42; 606/48; 606/51
(58) Field of Search .............................. 606/37, 41, 42, 606/45, 48–51

(56) References Cited

U.S. PATENT DOCUMENTS

| 4,427,006 A | 1/1984 | Nottke |
| 5,160,334 A | 11/1992 | Billings et al. |
| 5,269,780 A | 12/1993 | Roos |
| 5,376,089 A | 12/1994 | Smith |
| 5,573,424 A | 11/1996 | Poppe |
| 5,951,551 A | 9/1999 | Erlich |

(Continued)

FOREIGN PATENT DOCUMENTS

| DE | 199 43 792 A1 | 2/2001 |
| EP | 0 694 290 A2 | 1/1996 |
| EP | 1 050 277 A1 | 11/2000 |
| EP | 1 053 720 A1 | 11/2000 |
| EP | 1 112 720 A1 | 7/2001 |
| EP | 1 287 788 A1 | 3/2003 |
| WO | WO 96/37156 A1 | 11/1996 |
| WO | WO 98/38932 A1 | 9/1998 |
| WO | WO 00/53112 | 9/2000 |

*Primary Examiner*—Lee S Cohen
(74) *Attorney, Agent, or Firm*—Nixon & Vanderhye P.C.

(57) ABSTRACT

An electrosurgical system includes a generator for generating radio frequency (RF) power, and an electrosurgical instrument including at least three electrodes. The generator comprises an RF output stage having at least a pair of RF output lines, a power supply coupled to the output stage for supplying power to the output stage, and a controller capable of varying the RF power signal supplied to the output lines. The system also includes a selection circuit having at least three output connections each in electrical connection with a respective one of the at least three electrodes. This selection circuit operates to vary the coupling between the RF output stage and the three or more output connections. A switching device operable by the user causes the selection circuit to vary the electrode or electrodes to which RF power is supplied, and also causes the RF power signal supplied to at least one of the at least three output connections to vary depending on the electrode or electrodes to which RF power is supplied. In one arrangement of the selection circuit, one of the electrodes has no direct connection to the output stage of the generator and is connected via a capacitor to another of the electrodes.

20 Claims, 10 Drawing Sheets

U.S. PATENT DOCUMENTS

| | | |
|---|---|---|
| 5,976,132 A | 11/1999 | Morris |
| 6,174,309 B1 * | 1/2001 | Wrublewski et al. ......... 606/45 |
| 6,270,497 B1 | 8/2001 | Sekino et al. |
| 6,416,509 B1 | 7/2002 | Goble et al. |
| 6,679,882 B1 * | 1/2004 | Kornerup .................... 606/51 |
| 2003/0040744 A1 | 2/2003 | Latterell et al. |
| 2003/0073990 A1 | 4/2003 | Goble et al. |
| 2003/0163123 A1 | 8/2003 | Goble et al. |
| 2004/0006340 A1 * | 1/2004 | Latterell et al. .............. 606/48 |

* cited by examiner

ELECTROSURGICAL SYSTEM

CROSS REFERENCE TO RELATED APPLICATION

This is a continuation-in-part of U.S. application Ser. No. 10/228,284 filed Aug. 27, 2002, now U.S. Pat. No. 6,878, 148, which claims the benefit of U.S. provisional application Ser. No. 60/314,650, filed Aug. 27, 2001, the entire contents of both being incorporated herein by reference.

FIELD OF THE INVENTION

This invention relates to an electrosurgical system comprising an electrosurgical generator and a handpiece including electrosurgical electrodes. Such systems are commonly used for the cutting and/or coagulation of tissue in surgical intervention, most commonly in "keyhole" or minimally invasive surgery, but also in laparoscopic or "open" surgery.

BACKGROUND OF THE INVENTION

It is known to provide electrosurgical generators which provide different radio frequency (RF) power signals for cutting and coagulation, and also to switch between two different instruments, e.g. bipolar and monopolar instruments. In a first type of prior art system, it is also known to provide an electrosurgical instrument with a single electrode, and switching means on the instrument to connect the electrode alternately to either a cutting output or to a coagulating output from the generator. Examples of these types of instrument are to be seen in U.S. Pat. Nos. 4,427,006, 5,376,089 and 5,573,424.

Alternatively, in a second type of prior art system, it is known to provide an instrument with multiple electrodes, and to provide switching means on the instrument to be able to connect the power signal from the generator to different electrodes or combinations of electrodes. Examples of this type of instrument are to be seen in U.S. Pat. Nos. 5,269,780 and 5,951,551. The disadvantage of all of these prior art systems is that it is not possible to optimize both the signal supplied by the generator and the choice of electrodes. In the case of the first type of prior art system, the use of a single electrode means that its design must always be a compromise between designs suited to cutting and those suited to coagulation. In the case of the second type of prior art, the instrument uses the same output power signal from the generator for whichever combination of electrodes is deployed. U.S. Pat. No. 6,270,497 discloses a device which switches between coagulation and cutting operations, but which is relatively complicated in design.

It is an object of the present invention to provide an electrosurgical system which attempts to provide an optimized combination of electrodes in the handpiece and electrosurgical power signal from the generator, and which is relatively simple in operation.

SUMMARY OF THE INVENTION

The invention provides an electrosurgical system including a generator for generating radio frequency power, and an electrosurgical instrument including at least three electrodes, the generator comprising at least one source of radio frequency (RF) power, and the system also including a selection arrangement operable to vary the coupling between the at least one RF source and the at least three electrodes, the system further including a switching device operable to cause the selection arrangement to vary the electrode or electrodes to which RF power is supplied, the arrangement of the system being such that the RF power signal applied to at least one of the electrodes varies depending on the electrode or electrodes to which radio frequency power is supplied, and also such that one of the electrodes has no direct connection to the output stage of the generator and is connected via a capacitor to another of the electrodes.

In one preferred embodiment, the RF power source includes an RF output stage having at least a pair of RF output lines; the generator includes a controller capable of varying the RF power signal supplied to the output lines; the selection arrangement comprises a switching circuit having at least three output connections each in electrical connection with a respective one of the at least three electrodes, and is operable to vary the connections between the RF output lines and the output connections; and the switching device is operable to cause the RF power signal applied to at least one of the three or more output connections to vary depending on the electrode or electrodes to which radio frequency power is supplied.

The capacitor preferably has a value of between 1 and 10 nF. This arrangement can simplify the switching required, and/or free up additional switching capability for use in other circumstances. The switching circuit is preferably located within the generator, although it is conceivable that the switching circuit alternatively be located within the handpiece of the electrosurgical instrument.

In this way, the electrosurgical power signal employed can be optimised depending on the choice of electrodes, and similarly the electrodes can be designed specifically for the function they are chosen to perform. Preferably, the controller automatically adjusts the RF power supplied to at least one of the three or more output connections to limit the peak generator output voltage to at least a first value when a first combination of electrodes is selected by the switching circuit, and to at least a second value when a second combination of electrodes is selected by the switching circuit.

In one arrangement, the generator supplies RF power to at least three electrodes simultaneously, the output voltage being limited to a first peak value between a first combination of electrodes, and to a second peak value between a second combination of electrodes. This can be achieved by the generator having first and second output stages adapted to produce RF power for the first and second combination of electrodes respectively. Alternatively, and more simply, at least three of the electrodes are connected to respective other electrodes by capacitors, such that the peak voltage delivered by a single output stage is different between the first and second combination of electrodes.

In one arrangement two of the three or more electrodes are in the form of jaws adapted to grasp tissue therebetween, and the third electrode is mounted on one of the jaws, separated therefrom by an insulating member. The third electrode may be mounted on the internal or external face of one of the jaws, or even at the tip thereof. The third electrode may be mounted on one of the jaws in a recess therein, such that only a part of the electrode protrudes from the jaw. This type of arrangement applies to forceps or scissors-type instruments, suitable for grasping and/or cutting tissue.

Alternatively, at least one and preferably at least three of the electrodes is in the form of a hook. Hook and needle-type instruments are also common in Laparoscopic surgery, and may be employed in the present invention. Conveniently one of the hook electrodes extends distally beyond the other electrodes. Preferably the electrode which extends distally beyond the other electrodes is positioned centrally between the other electrodes.

In one construction at least one of the electrodes is longitudinally movable such that it can be extended and retracted with respect to the other electrodes. In this way tissue can be held in the gap formed between the retractable electrode and the other electrodes. As before, the longitudinally movable electrode is preferably positioned centrally between the other electrodes.

The invention further resides in an electrosurgical including a generator for generating radio frequency (RF) power, and an electrosurgical instrument including at least three electrodes, two of the at least three electrodes being in the form of jaws adapted to grasp tissue therebetween, and the third electrode being mounted on one of the jaws, separated therefrom by an insulating member, the generator comprising at least one source of RF power, and the system also including a selection circuit operable to vary the coupling between the at least one RF source and the at least three electrodes, the system further including a switching device operable to cause the selection circuit to vary the electrode or electrodes to which RF power is supplied, the arrangement being such that the RF signal applied to at least one of the electrodes varies depending on the electrode or electrodes to which RF power is supplied.

The invention further resides in an electrosurgical system including a generator for generating RF power, and an electrosurgical instrument including at least three electrodes, the generator comprising:

(i) an RF output stage having at least a pair of RF output lines, (ii) a power supply coupled to the output stage for supplying power to the output stage, and (iii) a controller capable of varying an RF signal supplied to the RF output lines, the electrosurgical instrument including a selection circuit having at least three output connections each in electrical connection with a respective one of the at least three electrodes, and operable to vary the connections between the RF output lines and the output connections, the system further including a switching device operable to send a signal to the selection circuit in order to vary the electrode or electrodes to which RF power is supplied, the switching device also causing the RF power signal supplied to at least one of at least three output connections to vary depending on the electrode or electrodes to which RF power is supplied.

According to another aspect, the invention resides in an electrosurgical system including a generator for generating radio frequency (RF) power, and an electrosurgical instrument including at least three electrodes, wherein the generator comprises an RF source having at least a pair of RF output lines, the RF source being operable to deliver RF power to said output lines at at least different first and second radio frequencies, wherein the system further includes a coupling stage for coupling RF power on said RF output lines to the electrodes, the coupling stage comprising: a first output circuit connected to a first pair of said electrodes and tuned to said first frequency, and a second output circuit connected to a second pair of said electrodes and tuned to said second frequency, and wherein the system includes means for varying the output frequency of said RF source to deliver RF power to the first and second output circuits at said first frequency or at said second frequency.

The invention will now be further described, by way of example only, with reference to the accompanying drawings.

DETAILED DESCRIPTION OF THE PREFERRED EMBODIMENTS OF THE INVENTION

Figure 1:
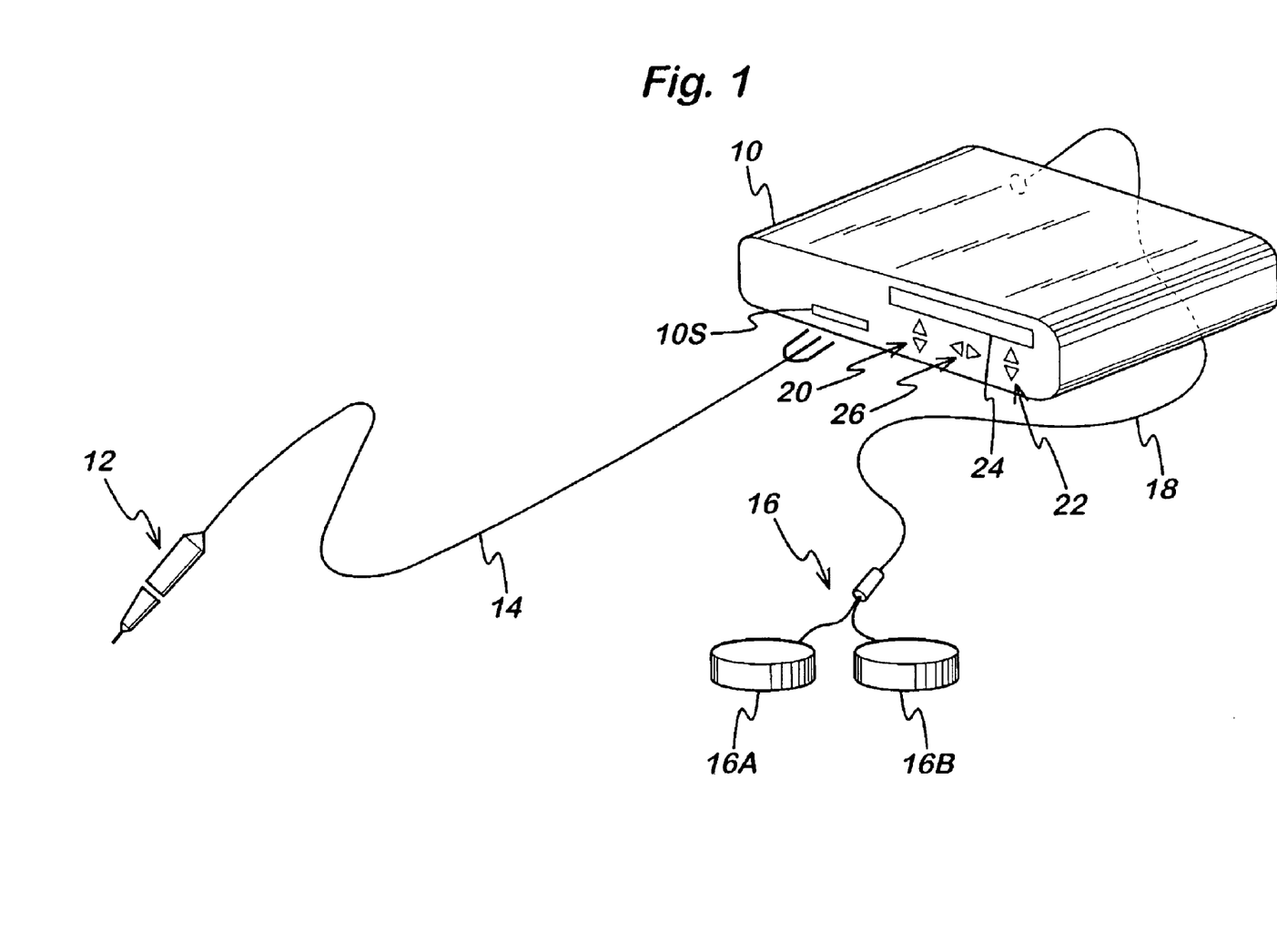
FIG. 1 is a schematic diagram of an electrosurgical system in accordance with the present invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
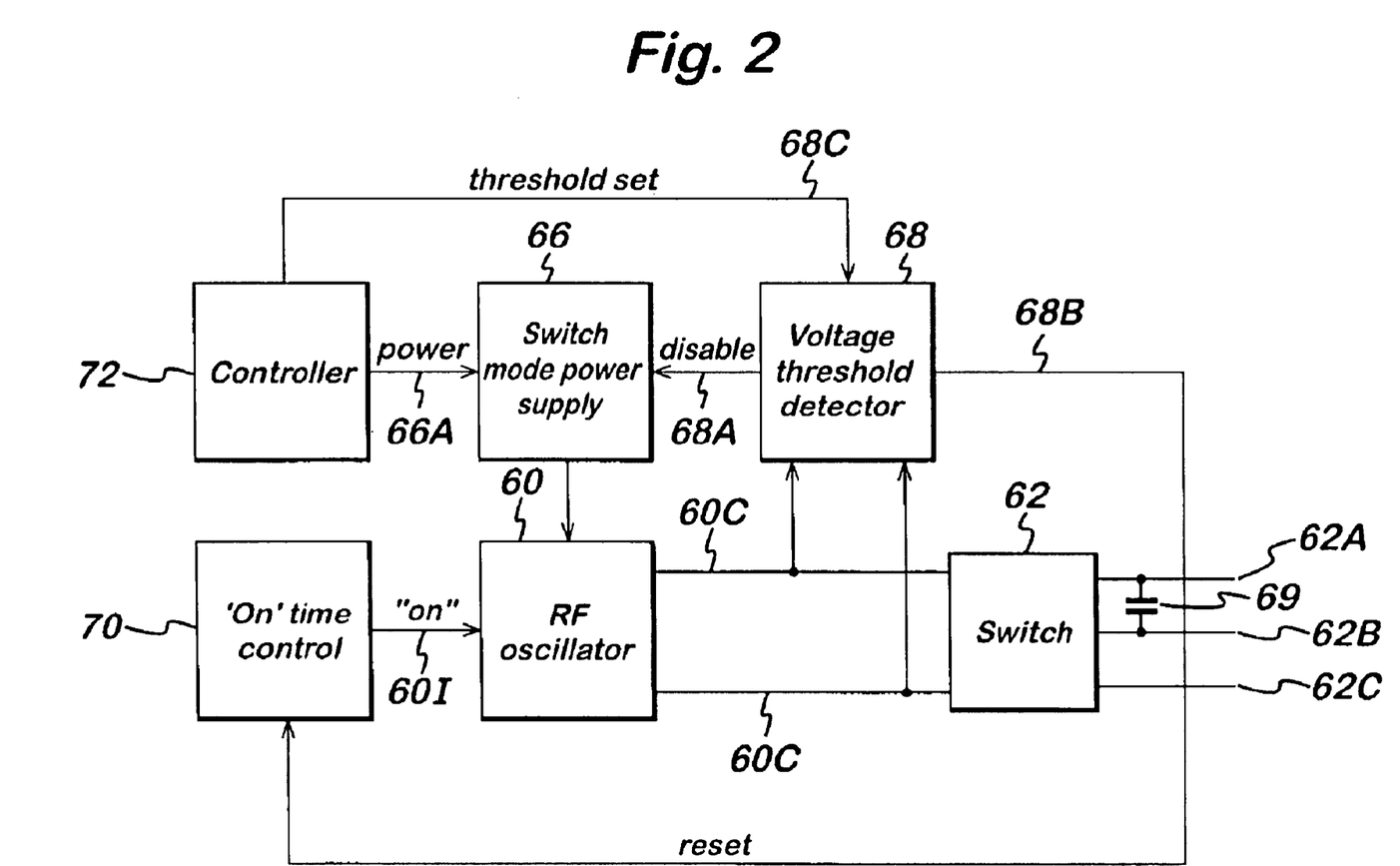
FIG. 2 is a block diagram of a generator forming part of the system of FIG. 1.

Referring to FIG. 2, the generator comprises a radio frequency (RF) output stage in the form of a power oscillator 60 having a pair of output lines 60C for coupling via switching circuit 62 to the instrument 12. Switching circuit 62 has three output connections 62A, 62B and 62C for connection to the electrodes of the instrument as will be described later. A capacitor 69 is connected between output connections 62A and 62B as shown. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a handpiece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each RE oscillation cycle. The power delivered to the load (not shown) depends partly on the supply voltage applied to the RF oscillator 60 from the switched mode power supply 66 and partly on the load impedance. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Figures 3, 3A:
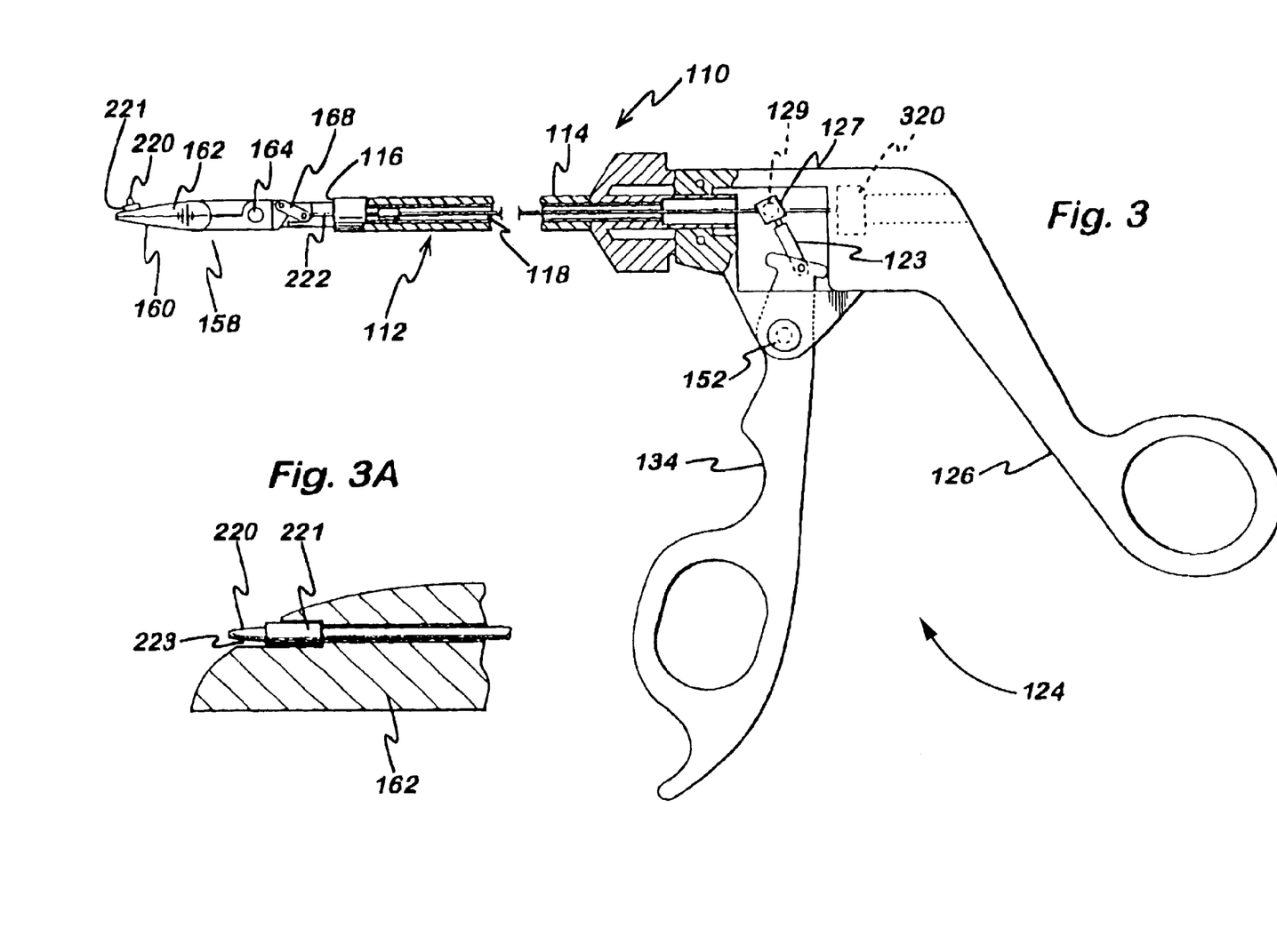
FIG. 3 is a schematic side view, shown partly in section, of a forceps-type instrument for use in the system of FIG. 1.
FIG. 3A is a sectional side view showing an alternative embodiment of jaw for the instrument of FIG. 3.

FIG. 3 shows one type of instrument 12 which can be connected to the generator 10. The device is a bipolar forceps shown generally at 110. The forceps has an elongated tubular member or shaft 112 with a proximal end 114, distal end 116, and a lumen 118 which extends for the entire length of the shaft. At the proximal end 114 of the shaft 112 is a scissors-type handle assembly 124 with a first handle 126 and a second handle 134. The second handle 134 is pivotable with respect to the first, about pivot pin 152. In a known design of actuation mechanism, the second handle 134 has a pin 123 affixed to the top thereof, such that movement of the handle causes a corresponding movement of a sphere 129 supported in a U-shaped cradle 127.

Figure 4:
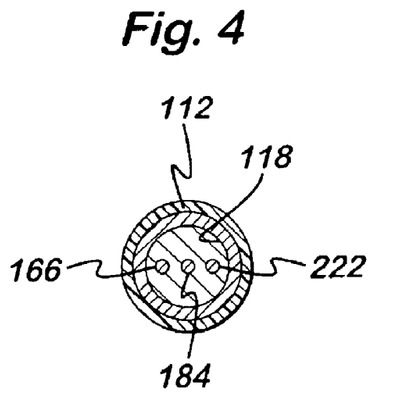
FIG. 4 is a cross-section of a shaft of the instrument of FIG. 3, FIGS. 5A and 5B are schematic views of the switching circuitry of FIG. 2, shown in first and second alternative conditions.

Fitted into the distal end 116 of the shaft 112 is a forceps jaw assembly 158 comprising a first jaw member 160 and a second jaw member 162, pivotally joined to each other by an insulated rivet 164. Jaw member 162 is provided with a cutting electrode 220, isolated from jaw member 162 by a ceramic insulator 221. As shown in FIG. 4, three rigid electrically conductive rods 166, 184 and 222, each covered with a layer of electrical insulation, extend through the lumen 118 of the shaft 112. The rods 166, 184 are pivotally connected to the respective jaw members 160, 162 by rigid links 168, whilst rod 222 is connected by means of a wire (not shown) to the electrode 220. The proximal ends of the rods 166, 184 and 222 extend from the tubular member through the sphere 129 and terminate in a connector 320. Output connections 62A, 62B and 62C from the generator 10 are thereby electrically connected to the rods 166, 184 and 222 respectively, via lead 14 and connector 320.

Figure 5A:
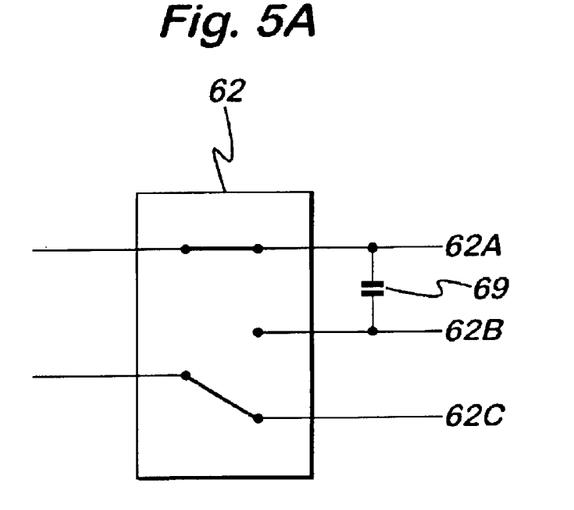

The operation of the instrument will now be described. When it is desired to operate the instrument 12 in a cutting mode, footswitch 16A is depressed which causes a signal to be sent to the controller 72 which sets the switching circuit 62 its "cut" position. This is illustrated in FIG. 5A, in which the signals from the oscillator 60 are connected between output connections 62A and 62C. This means that the RF power signal is applied between the cutting electrode 220 (via rod 222) and the jaw member 160 (via rod 166). Output connection 62B (and hence rod 184 and jaw member 162) has no direct connection to the generator, being connected solely via capacitor 69 to output connection 62A. The value of the capacitor 69 is typically 2.2 nF, and this is such that, in cutting mode, the output connection 62B is allowed to reach a similar potential to that of connection 62A.

At the same time as the controller 72 sets the switching circuit to the position in FIG. 5A, it also sends a signal via line 68C to the voltage threshold detector 68 to set the peak output voltage limit to a relatively high "cutting" level. The control of this cutting signal is described in more detail in EP 0754437, referred to earlier. In cutting mode, the output from the generator is a relatively high voltage, with a consequent low current level, and the impedance offered by the capacitor 69 is small in comparison with the impedance provided between the cutting electrode and the power tissue being treated.

Figure 5B:
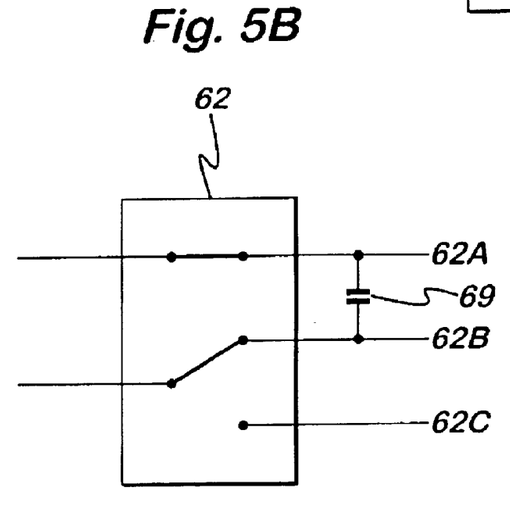

Alternatively, when it is desired to operate the instrument 12 in a coagulation mode, footswitch 16B is depressed which causes the controller 72 to set the switching circuit 62 to its "coag" state, as illustrated in FIG. 5B. In this set-up, the signals from the oscillator are connected between output connections 62A and 62B. This means that the RF signal is applied between the two jaw members 160 and 162 (via rods 166 and 184). At the same time the controller sends a signal to the voltage threshold detector 68 to set the peak output voltage limit to a relatively lower "coagulating" level, again as more particularly described in EP 0754437. In "coag" mode, the output from the generator is a relatively lower voltage, with a corresponding relatively higher current, and the impedance offered by the capacitor 69 is sufficient to maintain a potential difference between the output connections 62A and 62B. The capacitor 69 therefore allows sufficient voltage differential between the coagulating electrodes (160 and 162) to permit the coagulation of tissue to be performed.

It will be noted that in FIGS. 5A and 5B, only one switching element is required, with the connection between the generator and output connection 62A being maintained for both cutting and coagulation. The use of the capacitor 69 therefore simplifies the switching required, and/or frees up additional switching capability within the generator for use in other circumstances. It will also be appreciated that, although the capacitor 69 is shown in FIGS. 5A and 5B as being a part of the generator 10, it may alternatively be provided as a part of the instrument 12. In this way, different values of capacitor can be provided for different instruments, depending on their size and configuration.

It will be seen that not only is the RF power signal different for cutting and coagulation, but also the electrodes used to perform each operation. Cutting is performed using the relatively small cutting electrode 220, using the relatively large surface area of the jaw member 160 as the return electrode. Conversely, coagulation is performed, not using the cutting electrode, but using the first and second jaw members 160 and 162. In this way both the electrosurgical power signal and the choice of electrode can be optimized, depending on the function to be performed.

In alternative embodiments of the device of FIGS. 3 and 4, the cutting electrode 220 may be located at the tip of the jaw member 162, or even on the inside jaw face as opposed to the outside jaw face illustrated in FIG. 3. Alternatively, the cutting electrode 220 and the ceramic insulator 221 may be mounted on the jaw member 162 in a recess 223 provided thereon. This is the arrangement illustrated in FIG. 3a. The operation of the instrument will be the same, and the location of the cutting electrode may merely depend on the type of procedure undertaken.

Figure 6:
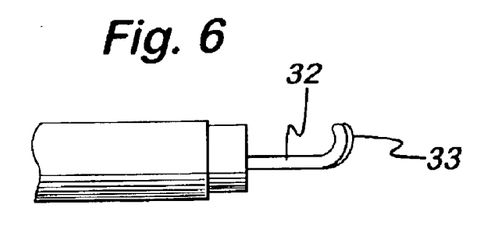
FIGS. 6 and 7 are side and plan views, respectively, of a part of an alternative instrument for use in the system of FIG. 1.
Figure 7:
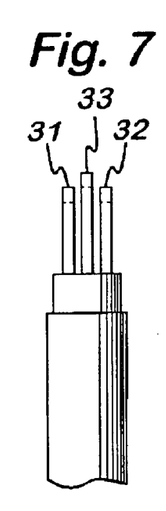

FIGS. 6 and 7 show an alternative embodiment in which the jaw members of the device of FIG. 3 are replaced by hook electrodes. These types of instrument are particularly suited to procedures such as Prostatectomy and Nephrectomy. First and second outside hook electrodes 31 and 32 are connected to output connections 62A and 62B respectively, whilst a central cutting hook electrode 33 is connected to output connection 62C. The cutting hook electrode protrudes slightly further forward than the outside electrodes 31 and 32, as shown in FIG. 6. As before, when the instrument is to be used for cutting, the switching circuit 62 is set to the state shown in FIG. 5A, and the cutting hook electrode 33 is energised with a cutting RF power signal, with one or both of the outside hook electrodes acting as the return electrode. When coagulation is desired, the switching circuit is set to the state shown in FIG. 5B such that a coagulating RF power signal is supplied to both of the outside hook electrodes 31 and 32.

Figure 7A:
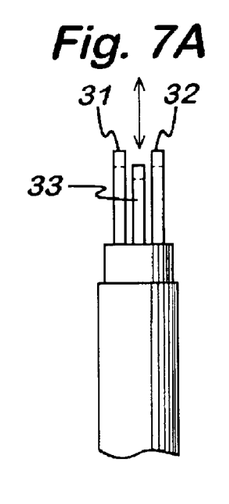
FIG. 7A is a plan view of an alternative embodiment of the instrument of FIGS. 6 and 7.

In further alternative embodiments of the invention, either the central cutting electrode or the outside electrodes can be made extendible and retractable, or the outside electrodes can be made jaw-like in order to spread or grasp tissue to be cut or coagulated. FIG. 7a shows a variation on the device of FIGS. 6 and 7 in which the central hook electrode 33 is movable longitudinally with respect to the outside electrodes 31 and 32. In FIG. 7a the central electrode is shown retracted behind the outside electrodes, such as would be the case when coagulating using the outside electrodes or cutting by pulling the tissue towards the central cutting electrode 33.

Figure 8:
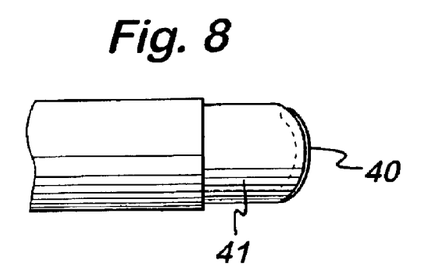
FIG. 8 is a side view of a part of a further alternative instrument for use in the system of FIG. 1, the instrument being shown in a retracted position.
Figure 9:
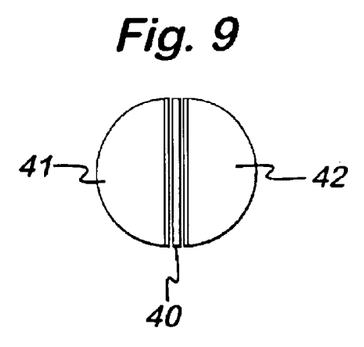
FIG. 9 is an end view of the instrument of FIG. 8.
Figure 10:
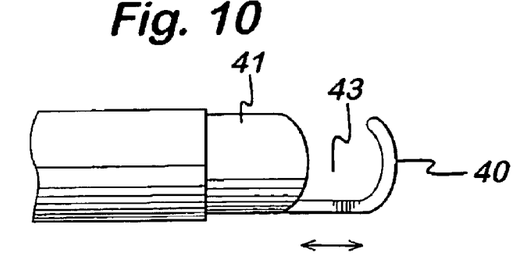
FIG. 10 is a side view of the instrument of FIG. 8, shown in an extended position.

In a further embodiment, illustrated in FIGS. 8 to 10, a central extendible hook electrode 40 is provided between stationary outside electrodes 41 and 42. In its retracted position, shown in FIG. 8, the central electrode protrudes only slightly beyond the outside electrodes 41 and 42. In this position, the instrument may be used as a tissue cutter, with the central electrode being supplied with a cutting RF power signal from the generator 10, and one or both of the outside electrodes acting as return electrodes. The central electrode may also be extended, as shown in FIG. 10, and then retracted to hold tissue in the gap 43 created between the central hook electrode 40 and the outside electrodes 41 and 42. By supplying a coagulating RF power signal to the outside electrodes (the switching circuit connecting the oscillator 60 to the output connections 62A and 62B as previously described), the tissue held in the gap 43 can be coagulated or desiccated. Alternatively, a cutting RF power signal is supplied to the central hook electrode 40 (the switching circuit connecting the oscillator 60 to the output connections 62A and 62C), and the electrode 40 is retracted in order to cut through the tissue in the gap 4.

Figure 11A:
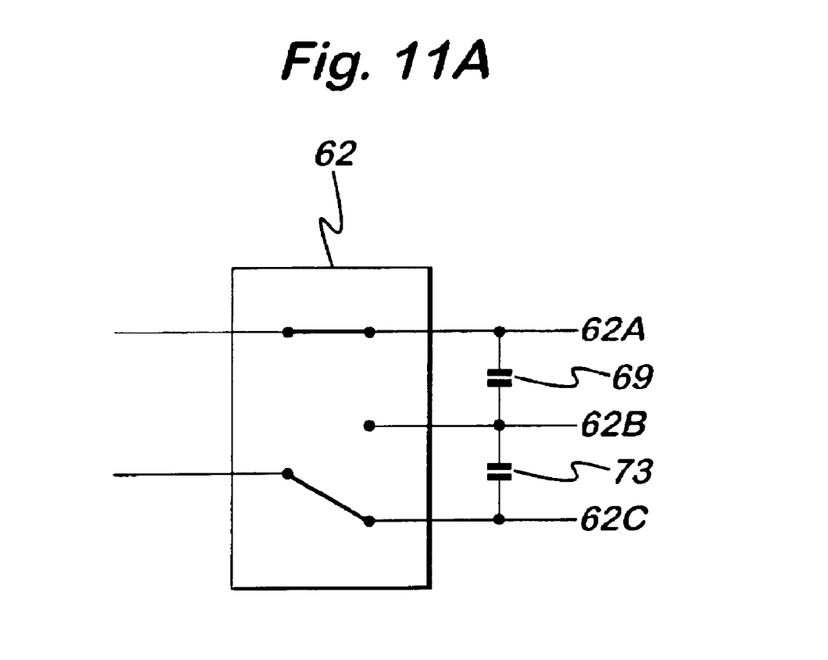
FIGS. 11A and 11B are schematic circuit diagrams showing an alternative embodiment of a device in accordance with the invention.
Figure 11B:
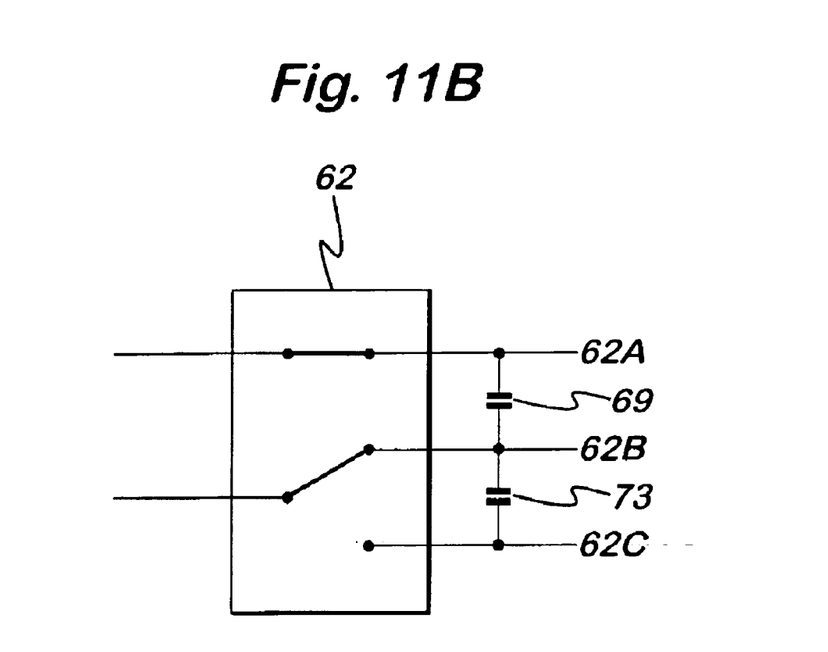

Referring to FIG. 11A, an arrangement is shown in which, in addition to the 2.2 nF capacitor 69 described previously between output connections 62A and 62B, an additional capacitor 73 is provided between output connections 62B and 62C. The value of this additional capacitor 73 is less than that for capacitor 69, typically 1.1 nF. The effect of this additional capacitor is as follows. When the switching circuit is as shown in FIG. 11A, the output stage of the generator is primarily connected between output connections 62A (and hence one of the coagulation electrodes) and 62C (and hence the cutting electrode). The relatively high potential difference between the cutting electrode and one or both of the coagulating electrodes will be such that the cutting of tissue can occur. However, the linking of the three electrodes by the capacitors 69 and 73 will have the effect that a relatively low potential difference will also be generated between output connections 62A and 62B (and hence the two coagulation electrodes). This will mean that as cutting of tissue is taking place, the tissue will simultaneously also be coagulated by the two coagulation electrodes. This simultaneous cutting and coagulation is an alternative to the sequential cutting and coagulation discussed previously. In FIG. 11B, the switching circuit is arranged such that the output stage of the generator is primarily connected between output connections 62A and 62B (and hence the two coagulation electrodes). This is the arrangement for the "coagulation only" setting of the device. The effect of the additional capacitor 73 will be that coagulation will occur between all three electrodes, with the cutting electrode becoming an additional coagulation electrode in the setting of FIG. 11B.

Figure 12:
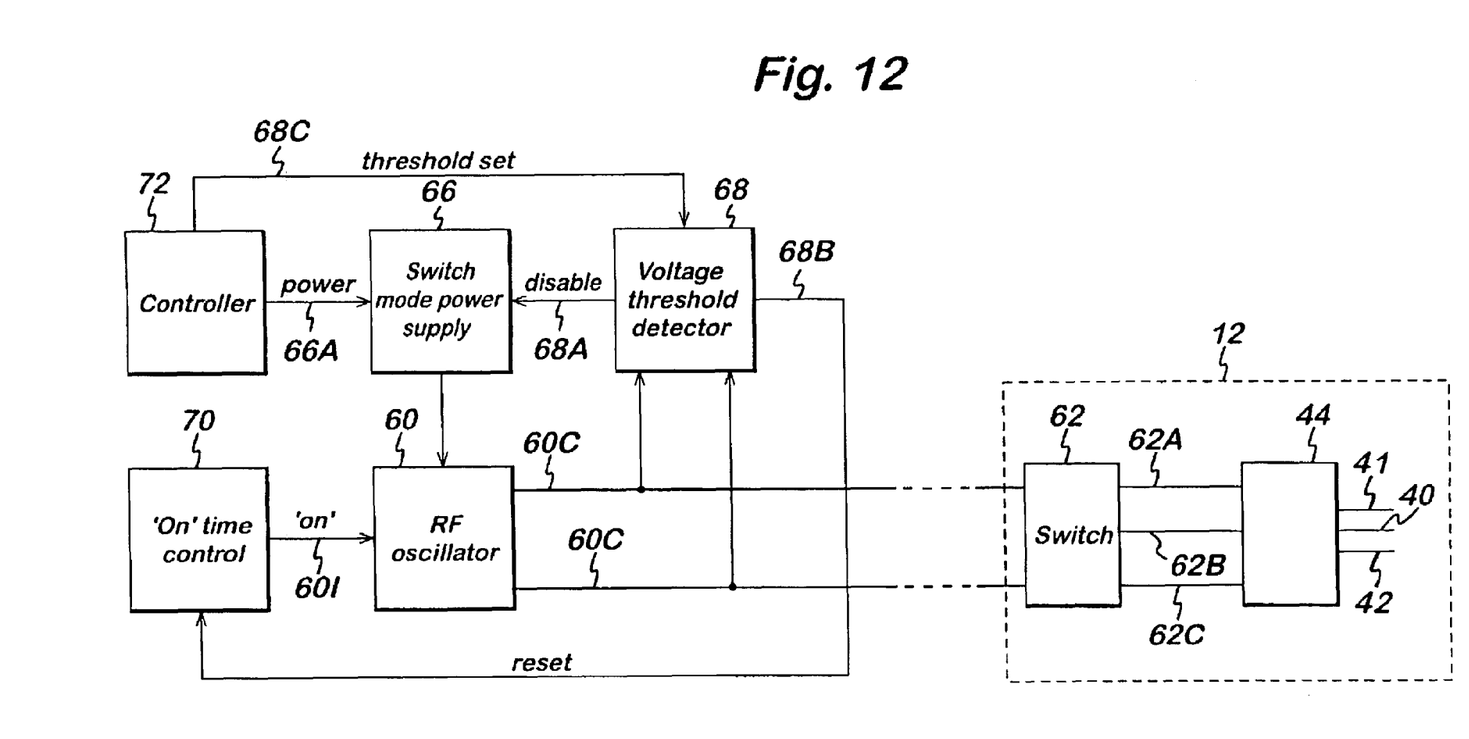
FIG. 12 is a schematic diagram of an alternative embodiment of electrosurgical system in accordance with the present invention.

FIG. 12 shows a generator circuit similar to that of FIG. 2, with like components being designated with like reference numerals. The major difference from the generator of FIG. 2 is that the switching circuit 62 is not present within the generator 10, but is located within the electrosurgical instrument 12. Thus the generator 10 has only two output connections 60C to which the instrument 12 is connected. The instrument 12 includes the switching circuit 62, which has output connections 62A, 62B and 62C as before, an instrument shaft 44, and electrodes 40, 41 and 42. By providing the switching circuit within the handpiece of the electrosurgical instrument 12, the need for switching within the generator is avoided, as is the need for three or more output connections from the generator 10. In other respects the system is as described above with reference to FIGS. 1 to 11B, and may take various forms, including the alternative instrument, electrode and switching circuit configurations set out above.

Figure 13:
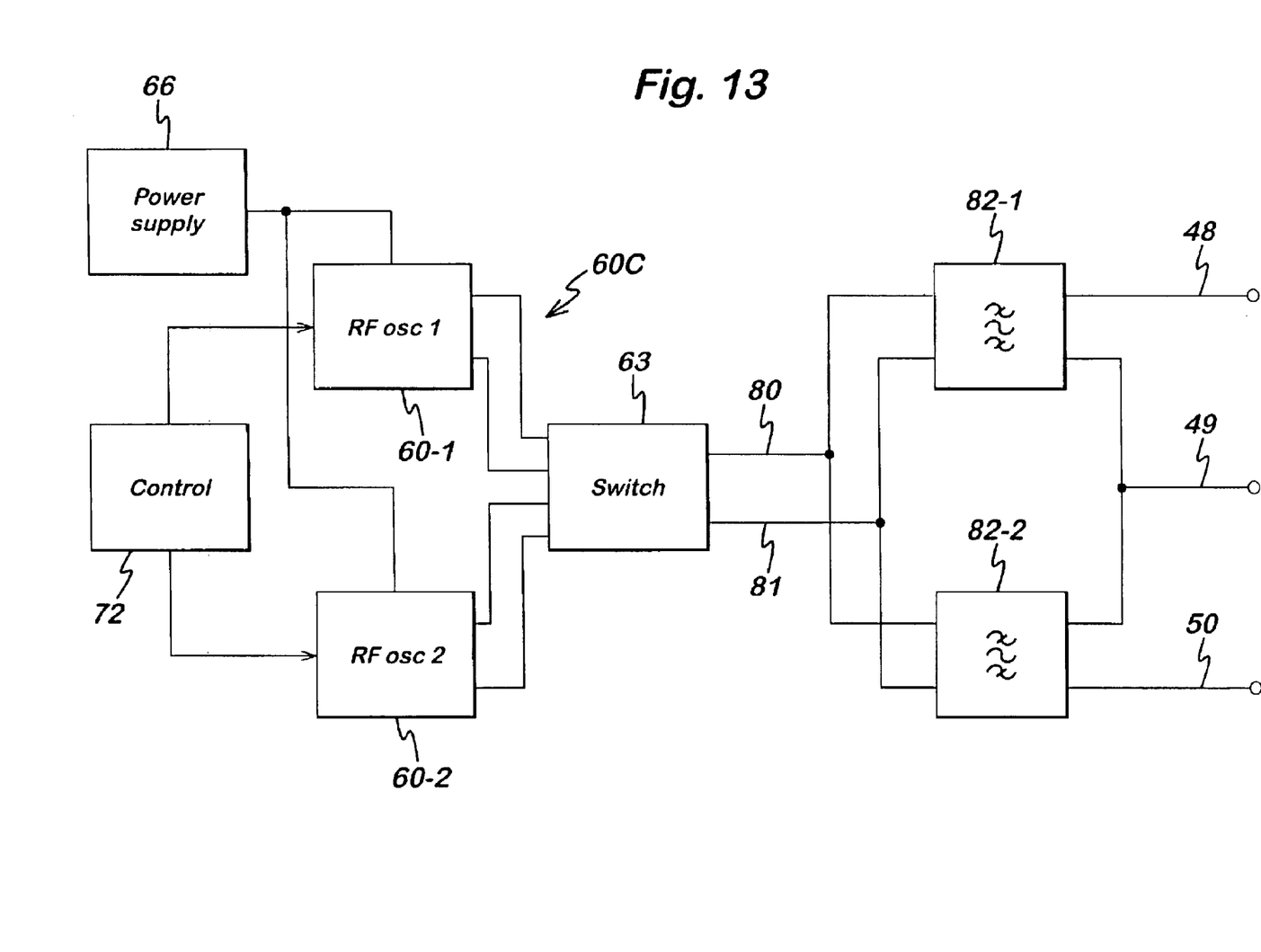
FIG. 13 is a schematic diagram of a further electrosurgical system in accordance with the invention.

Referring to FIG. 13, in an further alternative generator and instrument combination, two RF power oscillators 60-1 and 60-2 are powered from a common power supply 62 and are controlled by a common controller 72 to produce on respective output lines 60C an RF power signal suitable for cutting and an RF power signal suitable for coagulation. These signals may be fed to a switching circuit 63 for selecting the power signal from one oscillator 60-1 or the other oscillator 60-2 according to inputs from, for instance, foot switches, the selected power signal being transmitted on output connections 80, 81. In a blended mode, the switch is operated repeatedly at a predetermined rate to produce a blended output power signal across connections 80, 81. The power oscillators 60-1, 60-2 are operated at different frequencies, and the respective cut and coagulation signals are fed to the required electrodes by feeding the power signal on output connections 80, 81 to tuned circuits 82-1 and 82-2 tuned to the different frequencies. The outputs of the tuned circuits are coupled via electrode lines 48, 49 and 50 to the respective electrodes of the electrosurgical instrument. In this way, the cutting signal from oscillator 60-1 is fed to a cutting electrode 48 and a common electrode 49, whereas the coagulation signal from oscillator 60-2 is fed to a coagulation electrode 50 and the common electrode 49.

In the embodiment shown in FIG. 13, the connection between the electrosurgical generator and the electrosurgical instrument is typically provided by output connections 80 and 81, but the apportionment of circuit blocks between the generator and the instrument may be varied.

Figure 14A:
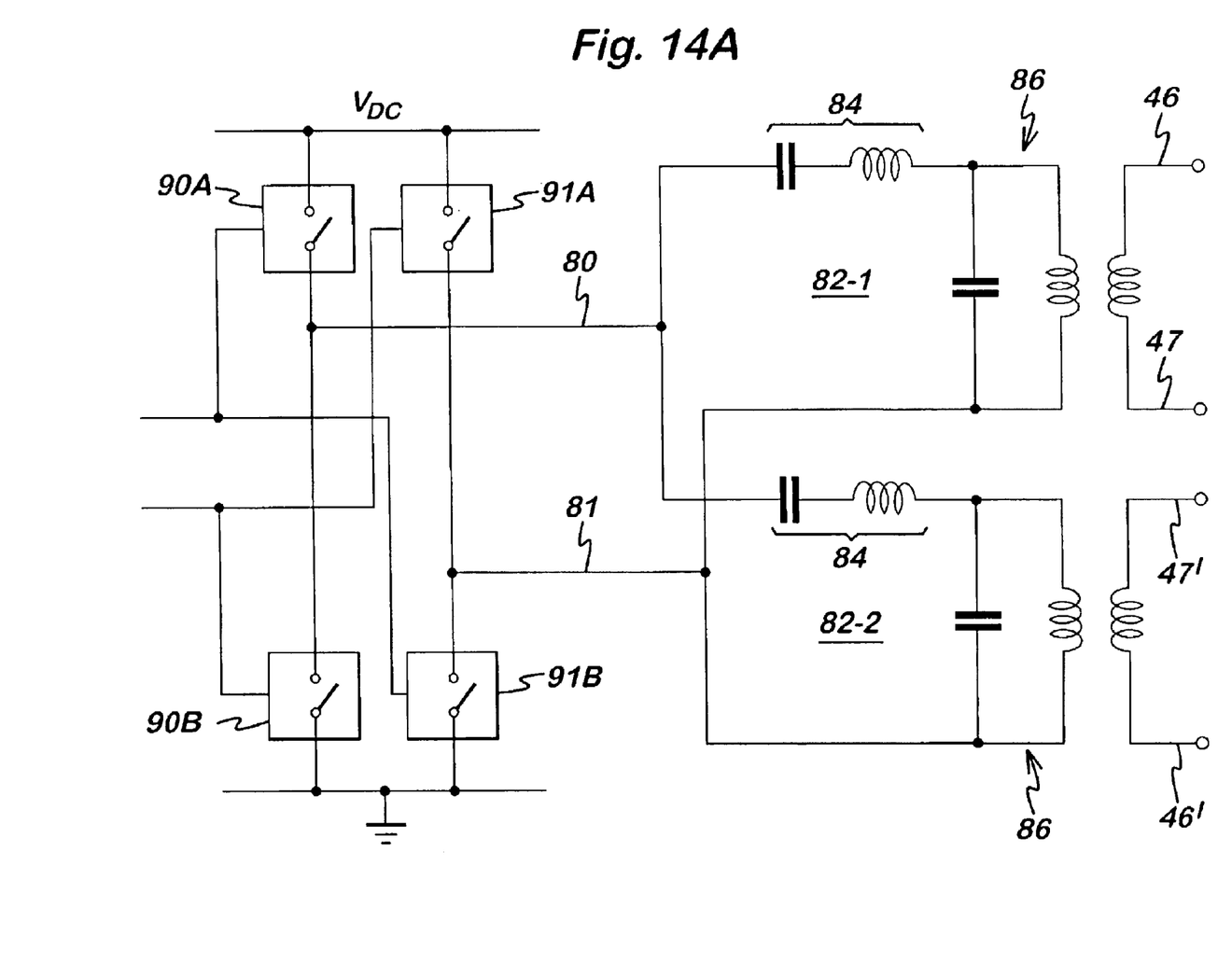
FIGS. 14A and 14B are circuit diagrams of alternative RF output stages of yet further embodiments of the invention.
Figure 14B:
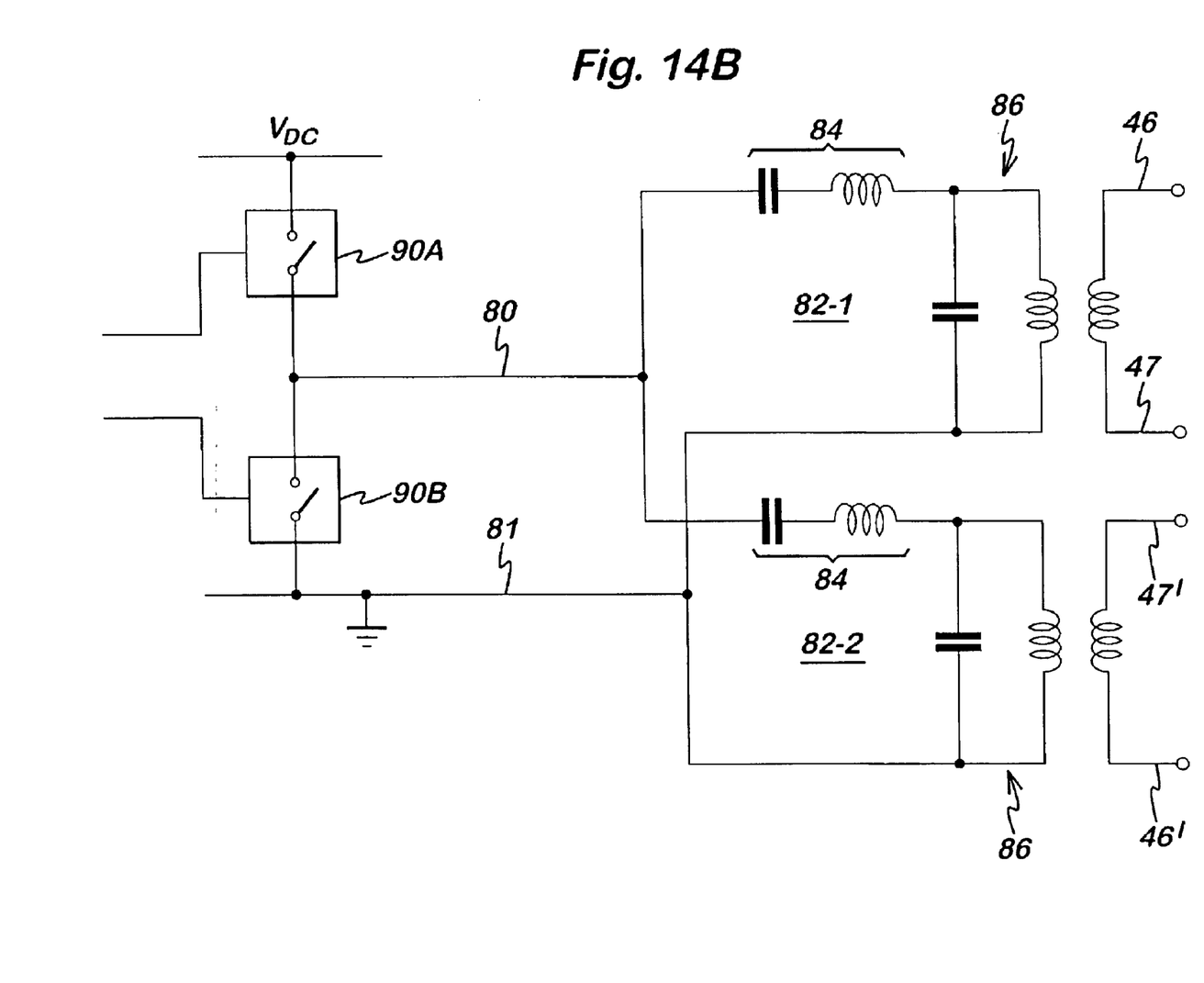

Further embodiments are shown in FIGS. 14A and 14B. These embodiments dispense with the need for a signal routing switch or switching circuit.

Referring to FIG. 14A, there are provided two tuned circuits 82-1 and 82-2 (as in FIG. 13), tuned to different frequencies. Each has a series-resonant inductor-capacitor pair 84 and a parallel-resonant inductor-capacitor pair 86, the latter being transformer-coupled to electrode output connections 46 and 47 on the one hand and 46' and 47' on the other hand. As in the embodiment of FIG. 13, each tuned circuit has two inputs, one of which is connected to a generator output connection 80 and the other of which is connected to a generator output connection 81. In this embodiment, the generator has an output stage comprising RF switches arranged in two oppositely acting push-pull pairs 90A, 90B and 91A, 91B. Typically these switches comprise power MOSFETS. Each switch 90A, 90B, 91A, 91B is connected to driver inputs 92, 93, as shown, which receive an RF drive signal which, for producing on the output connections 80, 81 an output having a cut waveform, is at one RF frequency, and, for producing a coagulation output on the output connections 80, 81, has a different RF frequency, these frequencies being, respectively, the resonant frequency of the resonant combinations 84, 86 of the first tuned circuit 82-1 and the resonant frequency of the corresponding resonant combinations of the other tuned circuit 82-2. As described above, the RF switches 90A, 90B, 91A and 91B of the generator output stage may be driven according to, for instance, a footswitch control to produce a cut output or a coagulation output. Again, additionally, a blended output may be produced in which the RF frequency alternates constantly between the two resonant frequencies of the tuned output circuits.

The embodiment of FIG. 14B is a modification of that of FIG. 14A, in which the generator output stage has a single push-pull pair of RF switches 90A, 90B and in which the tuned circuits each have one input connected to the junction between the switches 90A, 90B and the other input connected to ground.

More generally, it will be appreciated that other embodiments of generator and electrode can be envisioned without departing from the scope of the present invention. By employing three or more electrodes and selecting their coupling to the source of RF power, and also adjusting the RF power signal depending on which electrodes are being employed at any one time, the electrosurgical signal and the electrode configuration can be matched to optimum effect.

What is claimed is:

1. An electrosurgical system including a generator for generating radio frequency power, and an electrosurgical instrument including at least three electrodes, the generator comprising at least one source of radio frequency (RF) power, and the system also including a selection arrangement operable to vary the coupling between the at least one RF source and the at least three electrodes, the system further including a switching device operable to cause the selection arrangement to vary the electrode or electrodes to which RF power is supplied, the arrangement of the system being such that the RF power signal applied to at least one of the electrodes varies depending on the electrode or electrodes to which radio frequency power is supplied, and also such that one of the electrodes has no direct connection to the output stage of the generator and is connected via a capacitor to another of the electrodes.

2. A system according to claim 1, wherein:
the source of RF power includes an RF output stage having at least a pair of RF output lines;
the generator includes a controller capable of varying the RF power signal supplied to the output lines;
the selection arrangement comprises a switching circuit having at least three output connections each in electrical connection with a respective one of the at least three electrodes, and is operable to vary the connections between the RF output lines and the output connections; and
the switching device is operable to cause the RF power signal applied to at least one of the three or more output connections to vary depending on the electrode or electrodes to which radio frequency power is supplied.

3. A system according to claim 2, wherein the RF output stage of the generator is coupled to an RF driver and the controller is capable of varying an RF signal applied by the driver to the RF output stage.

4. A system according to claim 2, wherein the controller automatically adjusts the RF power supplied to at least one of said output connections to limit the peak generator output voltage to at least a first value when operation of the switching device causes RF power to be fed to a first combination of electrodes, and to at least a second value when operation of the switching device causes RF power to be fed to a second combination of electrodes.

5. A system according to claim 1, wherein the capacitor has a value of between 1 and 10 nF.

6. A system according to claim 1, wherein two of the three or more electrodes are in the form of jaws adapted to grasp tissue therebetween.

7. A system according to claim 6, wherein the third electrode is mounted on one of the jaws, separated therefrom by an insulating member.

8. A system according to claim 7, wherein the third electrode is mounted on an external face of one of the jaws.

9. A system according to claim 7, wherein the third electrode is mounted on an internal face of one of the jaws.

10. A system according to claim 7, wherein the third electrode is mounted at the tip of one of the jaws.

11. A system according to claim 1, wherein at least one of the electrodes is in the form of a hook.

12. A system according to claim 11, wherein at least one hook electrode extends distally beyond the other electrodes.

13. A system according to claim 12, wherein there is a centrally positioned electrode extending distally beyond the other electrodes.

14. A system according to claim 11, wherein at least three of the electrodes are in the form of a hook.

15. A system according to claim 1, wherein at least one of the electrodes is longitudinally movable such that it can be extended and retracted with respect to the other electrodes.

16. A system according to claim 15, wherein the longitudinally movable electrode is positioned centrally between the other electrodes.

17. A system according to claim 1, wherein the RF source and selection arrangement are such that the output stage supplies RF power to at least three electrodes simultaneously, the output voltage being limited to a first peak value between a first combination of electrodes, and to a second peak value between a second combination of electrodes.

18. A system according to claim 17, wherein, in a first mode of operation, a first one of the electrodes has no direct connection to the RF source of the generator and is connected via a capacitor to another of the electrodes, and, in a second mode of operation, a second one of the electrodes has no direct connection to the output stage of the generator and is connected via a capacitor to another of the electrodes.

19. A system according to claim 1, wherein the selection arrangement is located within the generator.

20. A system according to claim 1, wherein the selection arrangement is located within the electrosurgical instrument.

* * * * *